US006566512B1

(12) United States Patent
Sturley et al.

(10) Patent No.: US 6,566,512 B1
(45) Date of Patent: May 20, 2003

(54) ARV1, A PROTEIN INVOLVED IN STEROL UPTAKE AND STEROL HOMEOSTASIS IN THE BUDDING YEAST, S-CEREVISIAE, AND A FUNCTIONAL HUMAN ARV1

(75) Inventors: Stephen L. Sturley, New York, NY (US); Arthur H. Tinkelenberg, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 193 days.

(21) Appl. No.: 09/688,019

(22) Filed: Oct. 13, 2000

(51) Int. Cl.⁷ .......................... C07H 21/04; C12N 15/12
(52) U.S. Cl. ................ 536/23.5; 435/252.3; 435/254.3; 435/70.1; 435/71.1; 435/320; 435/325; 435/348; 435/419; 435/69.1; 530/350
(58) Field of Search ...................... 536/23.5; 435/252.3, 435/254.2, 70.1, 71.1, 320.1, 325, 348, 419, 69.1; 530/350

(56) References Cited

PUBLICATIONS

Bagnat, M. et al., Lipid Rafts Function in Biosynthetic Delivery of Proteins to the Cell Surface in Yeast. *Proc. Natl. Acad.. Sci. USA*, (Mar. 28, 2000) vol. 97:3254–3259.
Cross, F., Marker Swap Plasmids: Convenient Tools for Budding Yeast Molecular Genetics. *Yeast*, (1997) vol. 13: 647–653.
Corpet, F. et al., The ProDom Database of Protein Domain Families. *Nucleic Acids Research*, (1998) vol. 26: 323–326.
Crowley, J. et al., A Mutation in a Purported Regulatory Gene Affects Control of Sterol Uptake in *Saccharomyces cerevisiae*. *Journal of Bacteriology*, (Aug. 1998) vol. 180:4177–4183.
Erdeniz, N. et al., Cloning–FreePCR Based Allele Replacement Methods. *Genome Research*, (Dec. 1997) vol. 7: 1174–1183.
Hostager, B. et al., Recruitment of CD40 and Tumor Necrosis Factor Receptor–associated Factors 2 and 3 to Membrane Microdomains during CD40 Signaling. *The Journal of Biological Chemistry*, (Mar. 15, 2000) vol. 275: 15392–15398.
Kobayashi, T. et al., Late Endosomal Membranes Rich in Lisobisphosphatidic Acid Regulate Cholesterol Transport. *Nature Cell Biology*, (Jun. 1999) vol. 1:113–118.
Kranz, J. et al., Cloning by Function: An Alternative Approach for identifying Yeast Homologs of Genes from Other Organisms, *Proc. Natl. Acad. Sci USA*, (Sep. 1990) vol. 87:6629–6633.
Kutateladze, T, et al., Phosphatidylinositol 3–Phosphate Recognition by the FYVE Domain. *Molecular Cell*, (Jun. 1999) vol. 3: 805–811.

Loland, C.J. et al., Defining Proximity Relationships in the Tertiary Structure of the Dopamine Transporter. *The Journal of Biological Chemistry*, (Dec. 24, 1999) vol. 274: 36928–36934.
Schild, D. et al., Cloning of Three Human Multifunctional de novo Furine Biosynthetic Genes by Functional Complementation of Yeast Mutations. *Proc. Natl. Acad. Sci. USA*, (Apr. 1990) vol. 87: 2916–2920.
Wang, M.M. et al., Role of the Sterol Superlattice in the Partitioning of the Antifungal Drug Nystatin into Lipid Membranes. *Biochemistry*, (1998) vol. 37:11797–11805.
Warner, G, et al., Cell Toxicity Induced by Inhibition of Acyl Coenzyme A:Cholesterol Acyl–tranferase and Accumulation of Unesterified Cholesterol. *The Journal of Biological Chemistry*, (Mar. 17, 1995) vol. 270: 5772–5778.
Xu, X. et al., Lipoproteins Activate Acyl–coenzyme A:Cholesterol Acytransferase in Macro–phages Only After Cellular Cholesterol Pools Are Expanded to a Critical Threshold Level. *The Journal of Biological Chemistry*, (Sep. 15, 1991) vol. 266: 17040–17048.
Yang, H. et al., Functional Expression of a cDNA to Human Acyl–coenzyme A:Cholesterol Acyltransferase in Yeast. *The Journal of Biological Chemistry*, (Feb. 14, 1997) vol. 272: 3980–3985; and.
Yu. C. et al., Molecular Cloning Characterization of Two Isoforms of *Saccharomyces cerevisiae* Acyl–CoA:Sterol Acyltransferase. *The Journal of Biological Chemistry*, (Sep. 26, 1996) vol. 271:24157–24163.

*Primary Examiner*—Rebecca E. Prouty
*Assistant Examiner*—Sheridan Swope
(74) *Attorney, Agent, or Firm*—John P. White; Cooper & Dunham LLP

(57) ABSTRACT

This invention provides an isolated nucleic acid which encodes mammalian ACAT-Related Enzyme 2 Required for Viability protein (ARV1p), wherein the encoded ARV1p protein has the amino acid sequence set forth in FIG. 7. This invention provides an isolated nucleic acid which encodes yeast ACAT-Related Enzyme 2 Required for Viability protein (ARV1), wherein the encoded ARV1 protein has the amino acid sequence set forth in FIG. 5. This invention provides a purified mammalian ACAT-Related Enzyme 2 Required for Vialbility protein (ARV1p) having the amino acid sequence set forth in FIG. 7. This invention provides a purified yeast ACAT-Related Enzyme 2 Required for Vialbility protein (ARV1p) having the amino acid sequence set forth in FIG. 5. This invention provides a method for identifying a chemical compound which is capable of inhibiting or stimulating ACAT-Related Enzyme 2 Required for Viability protein (ARV1p) which is capable of inhibiting ARV1p. Methods of treatment using pharmaceutical compositions of the invention are also provided.

14 Claims, 8 Drawing Sheets

Figure 3A-3C
*a*
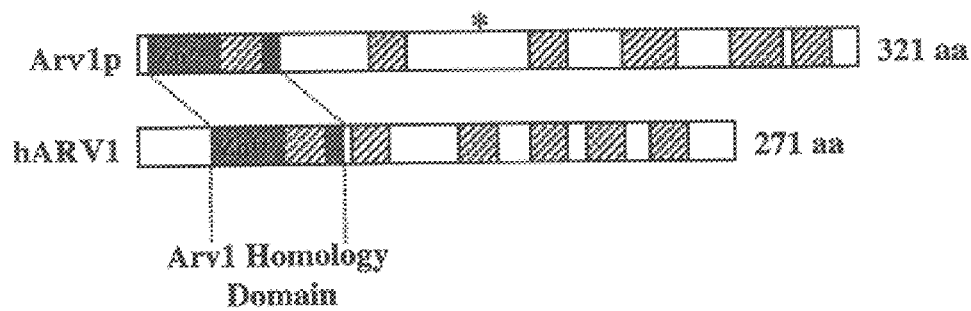
*b*
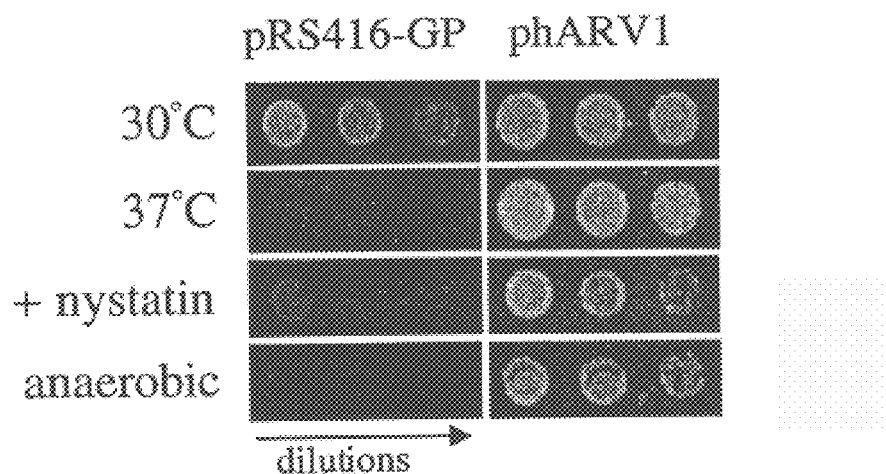

Figure 4

; ### from DNA Strider
; DNA sequence ARV1    966 b.p. complete sequence
;;

ATGATTTGCATAACGTGCATGGGCCCGTAGATTCCCTTATACAGTGTACTCGAATGACCACAT
TCAGCTGACAGATTG
TCCATATTGCCAAGAGACAGTAGACAAATATGTTGAGATAGATAATGTCCTGTTATTCATTGAT
TGCTTCTATTAAAAG
CAGGTGCATATAGACACTTGGTATTCAATGCTTTGGAATTGCATCTCTCAAAATATCCGAAAAG
AAAAGCGCTAAATGAT
TGCCAGTGTTGCGTGACTATACGCAAGCTTTGTTATTTAACGTAAAGAACTGGTTTGTAAATA
TGACCGGTAAATCG
CCTTTGGCTTCTACTATTATCATTCGAGATTTATTAACTGGGTTACTGAGGAGAGTAAATACA
TCTACTATTTGAACC
GTAACAATAATGATGGTAAGCTCATCATGCTTTCAAAAAAATTACCAGAGAGCTTCAAATGGGA
CTCGGCAATCATGCGC
AATACCATTACAAGTAAAGTGTTTACCTGGAGCCCACCAATACAATATCTTACTTTGCAAGTT
ATTGTATTCTTGACGT
TCTTTATTCCACACCTTTACCCAGTATTCATACTGAAAAAGTTGCATTGGAAGCACTATTCCG
TTTCTTCAAAGGATG
TCATATCATATACGATCTTATTATCGTACGGTGCCAAAATTTTCGATATTGATGTTGATATGG
CCTTATGATACTCTA
ATTTCGATGAGTATCATTAAGTGGGTAGCTAATCTCTATATTATTGAATCGTTGAAGATTGTAAC
TAATCTTCCTATTG
GAATATCATAAAGATTTTATAAGTGTGTCTTTATTACGATATTCATGGTTAAGCCAATACTT
ATAGTTTCGTGGCAA
AGTTTAACTTTTCAGTTATTAAGAATTAATACATCAGGAGTTATACTACTACAGAAGTC
AGGAACTTATTATTG
TTATAA
//

Figure 5

; ### from DNA Strider
; Protein sequence Arv1p    321 a.a. complete sequence
;;
MICITCMRPVDSLYTVYSNDHIQLTDCPYCQETVDKYVEIDNVLLFIDLLLLKAGAYRHLVFNALELHLSKY
PKRKALND
CQCLRDYTQALLFNVKNWFCKYDRLNRLWLLLSFEIYLTWVTEESKYIYYLNRNNNDGKLIMLSKKLPES
FKWDSAIMR
NTITSKVFTWSPPIQYLYFASYCILDVSLFHTFTQYFILKKLHWKHYSVSSKDVISYTILLSYGAKIFPILMLI
WPYDTL
ISMSIIKWVANLYIIESLKIVTNLSYWNIIKIFISVSLLRYFMVKPILIVFVAKFNFSVIKNLIHQEFILLLQKSGT
YLL
L
//

Figure 6

; ### from DNA Strider
; DNA sequence hARV1   816 b.p. complete sequence

ATGGGCAACGGCGGGGGAGCGGCCTGCAGCAGGGAAGCGTGGATGGGGTGGCAGGGACT
CCTACTGCCTC
GGCCTCCTGCCAGTACAGGTGCATCGAATGCAACCAGGAGGCCAAAGAGTTGTACGAGACTATA
ACCACGGTGTGCTGA
AGATAACCATCTGTAAATCCTGCCAGAAACCTGTAGACAAATATATCGAGTATGATCCTGTTAT
CATCTTGATTAATGCT
ATATTGTGCAAAGCTCAGGCCTACAGAGACATATTCTTTCAATACTCAAATAAATATCCATGGAA
AACTCTGCATATTTG
TTGCTTTGTGAAGCATACCTGAGGTGGTGGCAGCTTCAAGATTCCAACCAGAATACTGCCCTG
ATGACTTGATCAGAT
ATGCTAAGGAATGGGATTTCTATAGAATGTTTGCGATTGCTGTGCTTTAGAACAAACTGCCTATTT
ATTGGCATTTTACC
TTCCTGTGGGTAGAACGGCCCATGACGGCAAAAAAAGCCCAACTTCATTTTGCTGCTGAAAgC
TACGGAAAACTCTTGCTGCTGATTCCAGCTGTCATTGGGAACATGACTACACATCTGTGCCTCA
AACTCATTAAAGTAT
TGTTCTTACATCAAATTTTCAGGCAATTAGAGTGACCCTAAACATCAaCCGTAAGCTCTCCTTC
TTGGCCGTGTTGAGT
GGCTTACTGCTGAAAGCAtCATGGTCTACTTCTTCCAGAGTATGGAATGGGATGTTGGAAGTGAT
TATgCCATCTTTAA
ATCTCAGGACTTCTGA
//

Figure 7

; ### from DNA Strider
; Protein sequence hARV1p    271 a.a. complete sequence

MGNGGRSGLQQGKGNVDGVAATPTAASASCQYRCIECNQEAKELYRDYNHGVLKITICKSCQKPVDKYIE
YDPVIILINA
ILCKAQAYRHILFNTQINIHGKLCIFCLLCEAYLRWWQLQDSNQNTAPDDLIRYAKEWDFYRMFAIAALEQT
AYFIGIFT
FLWVERPMTAKKKPNFILLKALLLSSYGKLLLIPAVIWEHDYTSVCLKLIKVFVLTSNFQAIRVTLNINRK
LSFLAVLS
GLLLESIMVYFFQSMEWDVGSDYAIFKSQDF

SEQUENCE LISTING

<160> NUMBER OF SEQ ID NOS: 8

<210> SEQ ID NO 1
<211> LENGTH: 966
<212> TYPE: DNA
<213> ORGANISM: Human

<400> SEQUENCE: 1

```
atgatttgca taacgtgcat gcggcccgta gattcccttt atacagtgta ctcgaatgac      60
cacattcagc tgacagattg tccatattgc caagagacag tagacaaata tgttgagata     120
gataatgtcc tgttattcat tgatttgctt ctattaaaag caggtgcata tagacacttg     180
gtattcaatg ctttggaatt gcatctctca aaatatccga aaagaaaagc gctaaatgat     240
tgccagtgtt tgcgtgacta tacgcaagct ttgttattta acgtaaagaa ctggttttgt     300
aaatatgacc ggttaaatcg cctttggctt ctactattat cattcgagat ttatttaact     360
tgggttactg aggagagtaa atacatctac tatttgaacc gtaacaataa tgatggtaag     420
ctcatcatgc tttcaaaaaa attaccagag agcttcaaat gggactcggc aatcatgcgc     480
aataccatta caagtaaagt gtttacctgg agcccaccaa tacaatatct ttactttgca     540
agttattgta ttcttgacgt ttctttattc cacaccttta cccagtattt catactgaaa     600
aagttgcatt ggaagcacta ttccgtttct tcaaaggatg tcatatcata tacgatctta     660
ttatcgtacg gtgccaaaat ttttccgata ttgatgttga tatggcctta tgatactcta     720
atttcgatga gtatcattaa gtgggtagct aatctctata ttattgaatc gttgaagatt     780
gtaactaatc tttcctattg gaatatcata aagattttta taagtgtgtc tttattacga     840
tatttcatgg ttaagccaat acttatagtt ttcgtggcaa agtttaactt ttcagttatt     900
aagaatttaa tacatcagga gtttatacta ctactacaga agtcaggaac ttatttattg     960
``` ttataa                                                                 966

<210> SEQ ID NO 2
<211> LENGTH: 321
<212> TYPE: PRT
<213> ORGANISM: Human

<400> SEQUENCE: 2

Met Ile Cys Ile Thr Cys Met Arg Pro Val Asp Ser Leu Tyr Thr Val
1               5                   10                  15

Tyr Ser Asn Asp His Ile Gln Leu Thr Asp Cys Pro Tyr Cys Gln Glu
            20                  25                  30

Thr Val Asp Lys Tyr Val Glu Ile Asp Asn Val Leu Leu Phe Ile Asp
        35                  40                  45

Leu Leu Leu Leu Lys Ala Gly Ala Tyr Arg His Leu Val Phe Asn Ala
    50                  55                  60

Leu Glu Leu His Leu Ser Lys Tyr Pro Lys Arg Lys Ala Leu Asn Asp
65                  70                  75                  80

Cys Gln Cys Leu Arg Asp Tyr Thr Gln Ala Leu Leu Phe Asn Val Lys
                85                  90                  95

Asn Trp Phe Cys Lys Tyr Asp Arg Leu Asn Arg Leu Trp Leu Leu Leu
            100                 105                 110

Leu Ser Phe Glu Ile Tyr Leu Thr Trp Val Thr Glu Glu Ser Lys Tyr
        115                 120                 125

Ile Tyr Tyr Leu Asn Arg Asn Asn Asn Asp Gly Lys Leu Ile Met Leu
    130                 135                 140

Ser Lys Lys Leu Pro Glu Ser Phe Lys Trp Asp Ser Ala Ile Met Arg
145                 150                 155                 160

Asn Thr Ile Thr Ser Lys Val Phe Thr Trp Ser Pro Pro Ile Gln Tyr
                165                 170                 175

Leu Tyr Phe Ala Ser Tyr Cys Ile Leu Asp Val Ser Leu Phe His Thr
            180                 185                 190

Phe Thr Gln Tyr Phe Ile Leu Lys Leu His Trp Lys His Tyr Ser
        195                 200                 205

Val Ser Ser Lys Asp Val Ile Ser Tyr Thr Ile Leu Leu Ser Tyr Gly
    210                 215                 220

Ala Lys Ile Phe Pro Ile Leu Met Leu Ile Trp Pro Tyr Asp Thr Leu
225                 230                 235                 240

Ile Ser Met Ser Ile Lys Trp Val Ala Asn Leu Tyr Ile Ile Glu
                245                 250                 255

Ser Leu Lys Ile Val Thr Asn Leu Ser Tyr Trp Asn Ile Ile Lys Ile
            260                 265                 270

Phe Ile Ser Val Ser Leu Leu Arg Tyr Phe Met Val Lys Pro Ile Leu
        275                 280                 285

Ile Val Phe Val Ala Lys Phe Asn Phe Ser Val Ile Lys Asn Leu Ile
    290                 295                 300

His Gln Glu Phe Ile Leu Leu Gln Lys Ser Gly Thr Tyr Leu Leu
305                 310                 315                 320

Leu

<210> SEQ ID NO 3
<211> LENGTH: 815
<212> TYPE: DNA
<213> ORGANISM: Human

<400> SEQUENCE: 3

-continued

```
atgggcaacg gcgggcggag cggcctgcag caggggaagg ggaacgtgga tggggtggca      60
gcgactccta ctgctgcctc ggcctcctgc cagtacaggt gcatcgaatg caaccaggag     120
gccaaagagt tgtaccgaga ctataaccac ggtgtgctga agataaccat ctgtaaatcc     180
tgccagaaac ctgtagacaa atatatcgag tatgatcctg ttatcatctt gattaatgct     240
atattgtgca aagctcaggc ctacagacat attcttttca atactcaaat aaatatccat     300
ggaaaactct gcatattttg tttgctttgt gaagcatacc tgaggtggtg gcagcttcaa     360
gattccaacc agaatactgc ccctgatgac ttgatcagat atgctaagga atgggatttc     420
tatagaatgt ttgcgattgc tgctttagaa caaactgcct attttattgg catttttacc     480
ttcctgtggg tagaacggcc catgacggca aaaaaaaagc ccaacttcat tttgctgctg     540
aaagcattat tattatctag ctacggaaaa ctcttgctga ttccagctgt catttgggaa     600
catgactaca catctgtgtg cctcaaactc attaaagtat tgttcttac atcaaatttt      660 caggcaatta gagtgacccct aaacatcaac cgtaagctct ccttcttggc cgtgttgagt    720
ggttactgct ggaaagcatc atggtctact tcttccagag tatggaatgg gatgttggaa     780
gtgattatgc catcttaaa tctcaggact tctga                                 815
```

<210> SEQ ID NO 4
<211> LENGTH: 271
<212> TYPE: PRT
<213> ORGANISM: Human

<400> SEQUENCE: 4

```
Met Gly Asn Gly Gly Arg Ser Gly Leu Gln Gln Gly Lys Gly Asn Val
 1               5                  10                  15

Asp Gly Val Ala Ala Thr Pro Thr Ala Ala Ser Ala Ser Cys Gln Tyr
             20                  25                  30

Arg Cys Ile Glu Cys Asn Gln Glu Ala Lys Glu Leu Tyr Arg Asp Tyr
         35                  40                  45

Asn His Gly Val Leu Lys Ile Thr Ile Cys Lys Ser Cys Gln Lys Pro
     50                  55                  60

Val Asp Lys Tyr Ile Glu Tyr Asp Pro Val Ile Ile Leu Ile Asn Ala
 65                  70                  75                  80

Ile Leu Cys Lys Ala Gln Ala Tyr Arg His Ile Leu Phe Asn Thr Gln
                 85                  90                  95

Ile Asn Ile His Gly Lys Leu Cys Ile Phe Cys Leu Cys Glu Ala
            100                 105                 110

Tyr Leu Arg Trp Trp Gln Leu Gln Asp Ser Asn Gln Asn Thr Ala Pro
        115                 120                 125

Asp Asp Leu Ile Arg Tyr Ala Lys Glu Trp Asp Phe Tyr Arg Met Phe
    130                 135                 140

Ala Ile Ala Ala Leu Glu Gln Thr Ala Tyr Phe Ile Gly Ile Phe Thr
145                 150                 155                 160

Phe Leu Trp Val Glu Arg Pro Met Thr Ala Lys Lys Pro Asn Phe
                165                 170                 175

Ile Leu Leu Leu Lys Ala Leu Leu Ser Ser Tyr Gly Lys Leu Leu
            180                 185                 190

Leu Ile Pro Ala Val Ile Trp Glu His Asp Tyr Thr Ser Val Cys Leu
        195                 200                 205

Lys Leu Ile Lys Val Phe Val Leu Thr Ser Asn Phe Gln Ala Ile Arg
    210                 215                 220
```

```
Val Thr Leu Asn Ile Asn Arg Lys Leu Ser Phe Leu Ala Val Leu Ser
225                 230                 235                 240

Gly Leu Leu Glu Ser Ile Met Val Tyr Phe Phe Gln Ser Met Glu
            245                 250                 255

Trp Asp Val Gly Ser Asp Tyr Ala Ile Phe Lys Ser Gln Asp Phe
            260                 265                 270
```

<210> SEQ ID NO 5
<211> LENGTH: 61
<212> TYPE: PRT
<213> ORGANISM: Yeast Arv1p

<400> SEQUENCE: 5

```
Cys Ile Thr Cys Met Arg Pro Val Asp Ser Leu Tyr Thr Val Tyr Ser
1               5                   10                  15

Asn Asp His Ile Gln Leu Thr Asp Cys Pro Tyr Cys Gln Glu Thr Val
                20                  25                  30

Asp Lys Tyr Val Glu Ile Asp Asn Val Leu Leu Phe Ile Asp Leu Leu
            35                  40                  45

Leu Leu Lys Ala Gly Ala Tyr Arg His Leu Val Phe Asn
    50                  55                  60
```

<210> SEQ ID NO 6
<211> LENGTH: 61
<212> TYPE: PRT
<213> ORGANISM: Human ARV1

<400> SEQUENCE: 6

```
Cys Ile Glu Cys Asn Gln Glu Ala Lys Glu Leu Tyr Arg Asp Tyr Asn
1               5                   10                  15

His Gly Val Leu Lys Ile Thr Ile Cys Lys Ser Cys Gln Lys Pro Val
                20                  25                  30

Asp Lys Tyr Ile Glu Tyr Asp Pro Val Ile Leu Ile Asn Ala Ile
            35                  40                  45

Leu Cys Lys Ala Gln Ala Tyr Arg His Ile Leu Phe Asn
    50                  55                  60
```

<210> SEQ ID NO 7
<211> LENGTH: 61
<212> TYPE: PRT
<213> ORGANISM: C.elegans

<400> SEQUENCE: 7

```
Cys Val Asn Cys Gln Glu Phe Thr Ser Thr Leu Tyr Lys Lys Tyr Ser
1               5                   10                  15

Glu Gly Val Ile Arg Leu Thr Glu Cys Asp Asn Cys Gly Glu Val Val
                20                  25                  30

Asp Lys Tyr Ile Glu Tyr Asp Val Val Leu Val Ile Asp Leu Met
            35                  40                  45

Leu Gln Tyr Val Gln Ala Tyr Arg His Leu Leu Leu Asn
    50                  55                  60
```

<210> SEQ ID NO 8
<211> LENGTH: 61
<212> TYPE: PRT
<213> ORGANISM: A.thaliana

<400> SEQUENCE: 8

```
Cys Val Glu Cys Gly His Lys Val Lys Ser Leu Phe Ile Gln Tyr Ser
1               5                   10                  15
```

```
Pro Gly Asn Phe Arg Leu Met Lys Cys Glu Asn Cys Glu Glu Val Ala
            20                  25                  30

Asp Glu Tyr Val Glu Cys Glu Leu Leu Ile Ile Phe Ile Asp Leu Ile
            35                  40                  45

Leu His Lys Thr Lys Ala Tyr Arg His Leu Leu Tyr Asn
    50                  55                  60
```

//

ARV1, A PROTEIN INVOLVED IN STEROL UPTAKE AND STEROL HOMEOSTASIS IN THE BUDDING YEAST, S-CEREVISIAE, AND A FUNCTIONAL HUMAN ARV1

The invention disclosed was herein made in the course of work under NIH Research Grant Nos. DK54320 and GM62104 and NIH Training Grant No. DK07715. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Sterols are essential structural and regulatory components of eukaryotic cellular membranes[1,2]. However, cholesterol over-accumulation is cytotoxic[3] necessitating mechanisms to maintain this metabolite at appropriate levels. A pivotal component of this homeostasis is the esterification of free sterol by acyl-coenzyme A (CoA): cholesterol O-acyltransferase (ACAT)[4,5]. Indeed, the inhibition of ACAT in sterol-loaded cells induces cell death when extracellular sterol acceptors such as high density lipoproteins are absent[6]. Sterols are maintained at a high concentration in the plasma membrane (PM) relative to the endoplasmic reticulum (ER), where ACAT resides. Therefore, intracellular sterol redistribution between membranes and its subsequent esterification are critical aspects of lipid homeostasis. To identify genes that mediate sterol trafficking, we screened for yeast mutants that were inviable in the absence of sterol esterification. Mutations in the novel gene, ARV1, alter intracellular sterol transport, render cells nystatin sensitive, temperature sensitive, anaerobically inviable, and defective in sterol uptake. Human ARV1, a predicted ortholog of yeast ARV1, complements the defects associated with deletion of the yeast gene. We propose that ARV1 is a novel mediator of eukaryotic sterol homeostasis.

Intracellular sterol esterification plays a critical role in maintaining cellular free sterol below toxic levels. Trafficking of sterol to ACAT is critical for this homeostasis. In order to identify genes involved in sterol trafficking, we screened for mutants of budding yeast (*Saccharomyces cerevisiae*) that require sterol esterification for viability. We have identified a novel yeast gene, ARV1 (termed 'arv' for 'ARE2 Required for Viability') that is essential when the otherwise dispensable yeast ACAT-homologous genes, ARE1 and ARE2, have been deleted from the genome. We have identified a human homolog, hARV1, which rescues yeast arv1 deletion mutants.

Arv1 mutant cells are temperature sensitive and nystatin sensitive, suggesting elevated free sterol. Arv1 cells are anaerobically inviable, suggesting a critical need for Arv1p when cells must obtain sterol from extracellular sources. Arv1 cells accumulate 50% of control levels of exogenously supplied C14 cholesterol, suggesting Arv1p may facilitate exogenous sterol transport. The Arv1p amino acid sequence predicts a novel transmembrane protein with high similarity to entries in the database from C. elegans and human. We identified full length cDNA clones corresponding to hARV1. hARV1 yeast expression plasmids were constructed and found to rescue arv1 deletion strains, including temperature sensitivity as well as anaerobic inviability. We propose that hARV1 in human cells might play a similar role to that of Arv1p in yeast, protecting them when intracellular sterol levels are too high or when ACAT activity is insufficient.

This invention provides an isolated nucleic acid which encodes mammalian ACAT-Related Enzyme 2 Required for Viability protein (ARV1p), wherein the encoded ARV1p protein has the amino acid sequence set forth in FIG. 7.

SUMMARY OF THE INVENTION

This invention provides an isolated nucleic acid which encodes mammalian ACAT-Related Enzyme 2 Required for Viability protein (ARV1p), wherein the encoded ARV1p protein has the amino acid sequence set forth in FIG. 7.

This invention provides an isolated nucleic acid which encodes yeast ACAT-Related Enzyme 2 Required for Viability protein (ARV1), wherein the encoded ARV1 protein has the amino acid sequence set forth in FIG. 5.

This invention provides a purified mammalian ACAT-Related Enzyme 2 Required for Vialbility protein (ARV1p) having the amino acid sequence set forth in FIG. 7.

This invention provides a purified yeast ACAT-Related Enzyme 2 Required for Vialbility protein (ARV1p) having the amino acid sequence set forth in FIG. 5.

This invention provides an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 7.

This invention provides an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 5.

This invention provides a method for identifying a chemical compound which is capable of inhibiting ACAT-Related Enzyme 2 Required for Viability protein (ARV1p) which comprises: (a) contacting an isolated ARV1p with the chemical compound under conditions permitting an effect to occur upon contact between the ARV1p and the chemical compound; and (b) determining whether the chemical compound inhibits the activity of the ARV1p so as to identify a chemical compound which is capable of inhibiting ARV1p.

This invention provides a method for identifying a chemical compound which is capable of stimulating ACAT-Related Enzyme 2 Required for Viability protein (ARV1p) which comprises: (a) contacting an isolated ARV1p with the chemical compound under conditions permitting an effect to occur upon contact between the ARV1p and the chemical compound; and (b) determining whether the chemical compound stimulates the activity of the ARV1p so as to identify a chemical compound which is capable of stimulating ARV1p.

This invention provides a pharmaceutical composition comprising ARV1 protein having the amino acid sequence set forth in FIG. 7 and a pharmaceutically acceptable carrier.

This invention provides a method of treating a subject who has a disease wherein cellular sterol transport or sterol uptake are defective comprising administering a pharmaceutical composition comprising ARV1 protein having the amino acid sequence set forth in FIG. 7 and a pharmaceutically acceptable carrier to the subject so as to restore the sterol transport, sterol uptake or sterol distribution.

This invention provides a method for determining whether elevated levels of intracellular sterol in absence of sterol esterification in a subject are due to ARV1 mutation which comprises: (a) obtaining a nucleic acid sample from the subject; (b) comparing the nucleic acid from the sample with the isolated nucleic acid which encodes mammalian ACAT-Related Enzyme 2 Required for Viability protein (ARV1p), wherein the encoded ARV1p protein has the amino acid sequence set forth in FIG. 7; and (c) determining whether the nucleic acid from the sample of step (a) differs from the isolated nucleic acid encodes mammalian ARV1p, a difference in the nucleic acid from the isolated nucleic acid which encodes ARV1p indicating presence of a mutation in the nucleic acid encoding ARV1 from the sample.

This invention provides a method for determining whether elevated levels of intracellular sterol in absence of sterol esterification in a subject are due to ARV1 mutation which comprises: (a) obtaining nucleic acid from a sample from the subject; and (b) contacting the nucleic acid of step (a) with an isolated nucleic acid sequence encoding a mutant ARV1 under conditions permitting binding of any nucleic acid from the sample to the nucleic acid sequence encoding a mutant ARV1 so as to form a complex, formation of the complex indicating presence of a mutation in the nucleic acid encoding ARV1 from the sample.

This invention provides a method for treating a subject who has an imbalance in cell sterol levels due to a defect in sterol esterification which comprises introducing an isolated nucleic acid which encodes mammalian ACAT-Related Enzyme 2 Required for Viability protein (ARV1p), wherein the encoded ARV1p protein has the amino acid sequence set forth in FIG. 7, into cells of the subject under conditions such that the nucleic acid expresses ARV1p and the cells obtain sterol from an extracellular source, so as to thereby treat the subject.

This invention provides a method for treating a subject who has an imbalance in sterol levels in cells due to a defect in sterol esterification which comprises administering ARV1p to the subject, such that the ARV1p transports to the cells extracellular sterol, so as to thereby treat the subject.

This invention provides a transgenic nonhuman mammal comprising an isolated nucleic acid which encodes mammalian ACAT-Related Enzyme 2 Required for Viability protein (ARV1p), wherein the encoded ARV1p protein has the amino acid sequence set forth in FIG. 7.

This invention provides a transgenic nonhuman mammal comprising an isolated nucleic acid which encodes mammalian ACAT-Related Enzyme 2 Required for Viability protein (ARV1p), wherein the encoded ARV1p protein has the amino acid sequence set forth in FIG. 7 which is mutated.

This invention provides an antibody directed to an epitope of a purified mammalian ARV1p having the amino acid sequence set forth in FIG. 7.

This invention provides a plant producing seeds whose lipid oils content is altered from the wild-type lipid oils content by a change in the expression of nucleic acid which encodes human ARV1 or plant ARV1.

This invention provides a plant seed whose lipid oils content is altered from the wild-type lipid oils content by a change in the expression of nucleic acid which encode human ARV1 or plant ARV1.

This invention provides a method of altering lipid oils content of a plant seed which comprises introducing into the nucleic acid of the plant seed an isolated nucleic acid encoding plant ARV1p, wherein the encoded plant ARV1p differs from the wild-type plant ARV1, such that the lipid oils content of the plant seed is altered.

This invention provides a pharmaceutical composition comprising lipid oils of a plant seed whose lipid oils content is altered from the wild-type lipid oils content of the plant seed by a change in the expression of nucleic acid which encode ARV1 and a pharmaceutically acceptable carrier.

This invention provides a method for identifying a chemical compound which has antifungal activity which comprises: (a) contacting a yeast cell comprising an isolated nucleic acid which encodes yeast ACAT-Related Enzyme 2 Required for Viability protein (ARV1p), wherein the encoded ARV1p protein is a deletion mutant with the chemical compound under conditions permitting an effect to occur upon contact between the yeast cell and the chemical compound; and (b) determining whether the chemical compound inhibits yeast ARV1p so as to identify a chemical compound which has antifungal activity. The effect may be alteration of intracellular sterol transport, sensitivity to the compound, temperature sensitivity, anaerobic inviability, or a defect in sterol uptake.

BRIEF DESCRIPTION OF THE FIGURES

FIG. 1A, Temperature and nystatin sensitivity. 5-fold dilutions of cells were grown as indicated for three days on YEPD +/–5 $\mu$g/ml nystatin (10 mg/ml in propylene glycol). FIG. 1B, Characterization of sterol levels. Cells were labeled with [$^3$H] acetate and lipids extracted and analyzed by TLC. Data from three independent assays of two strains of each genotype is expressed as mean ratio over wild-type (±SEM; statistical significance by paired t-tests, *p<0.05 or **p<0.01 compared to wild-type). Hatched bars wild-type, gray bars= arv1D. FIG. 1C, Subcellular sterol accumulation. Cell membrane preparations were subjected to subcellular fractionation. Lipid composition is presented as ratio of [$^3$H]acetate in sterol and [$^{14}$C]oleate in phospholipids (top panels). Hatched bars=wild-type, gray bars=arv1D. Note scale differences between the upper panels. Fractions were characterized with specific antibodies against the plasma membrane ATPase (Pma1p, provided by Amy Chang), and 100 kDa subunit of integral vacuolar membrane H$^+$ATPase (Vph1p, Molecular Probes). Bottom panels show densitometry analysis of western blots expressed as percentage of total arbitrary units (Pma1p; closed boxes, Vph1p; open triangles). The integral ER membrane protein, dolichol phosphate mannose synthase cofractionated with Vph1p.

FIG. 2A, Anaerobic growth. 5-fold dilutions of cells were inoculated onto YEPD media supplemented to 20 mg/ml ergosterol and 0.5% Tween 80 as an oleate source [2 mg/ml ergosterol in Tween 80:ethanol (1:1)] and incubated for three days. FIG. 2B, Analysis of sterol uptake. Accumulation of [$^{14}$C] cholesterol was measured in three independent assays of two strains of each genotype. ** p<0.01 compared to wild-type.

FIGS. 3A–3C Isolation of hARV1. FIG. 3A, Identification of Arv1p homologs and the Arv1 Homology Domain (AHD, ProDom PD038388[18]). Alignment[31] of predicted NH$_2$-terminal AHDs of yeast Arv1p and human, *Caenorhabditis elegans*, and *Arabidopsis thaliana* database entries (AA461156, CAA88728, and CAB77721, respectively). Invariant (bold) and similar residues (+) are displayed; % identity compared to Arv1p indicated. FIG. 3B, Arv1p and hARV1 predicted structural features. The AHD encompassing the putative zinc-binding motif (Zn$^{++}$) is denoted by grey shading and predicted transmembrane domains[32] are indicated by striped boxes. The asterisk indicates the position of the stop codon in the arv1-1 allele. FIG. 3C, Rescue of arv1D mutants by expression of hARV1. arv1D strains with indicated plasmids were grown for two days on media with 3% galactose.

FIG. 4 DNA sequence encoding yeast ARV1 protein. The 966 b.p. encode ARV1 protein.

FIG. 5 Yeast ARV1p protein. The yeast ARV1 protein is a 321 amino acid protein.

FIG. 6 DNA sequence encoding human ARV1 protein, hARV1. The 816 b.p. encode hARV1 protein.

FIG. 7 Human ARV1p protein. The human ARV1 protein, hARV1, is a 271 amino acid protein.

DETAILED DESCRIPTION OF THE INVENTION

Figure 1A:
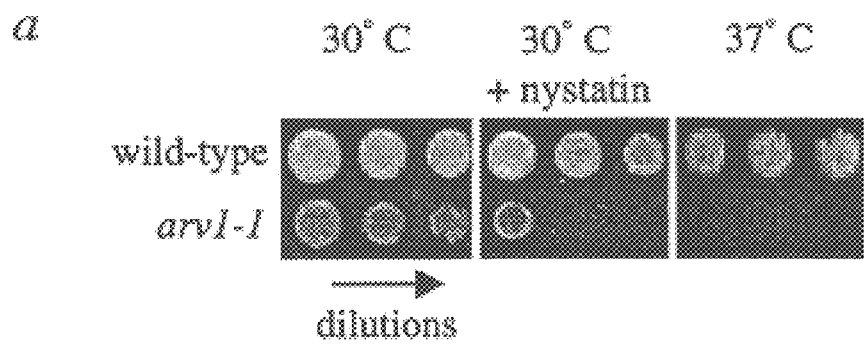
FIGS. 1A–1C arv1 mutant phenotypes.

Human ARV1 is a Functional Homolog of a Yeast Gene that Is Essential in the Absence of Sterol Esterification Cells precisely regulate the lipid content of their organelles and membranes. Aberrant cellular lipid homeostasis underlies the debilitating neurodegenerative disorder, Niemann-Pick Type C disease, where LDL-derived cholesterol accumulates in lysosomes. The biochemical function of the recently-identified NPC1 protein has not been elucidated, although NPC fibroblasts show a number of phenotypes suggestive of a defect in retroendocytic trafficking of specific cargoes, particularly plasma membrane lipids (cholesterol and sphingomyelin). In an effort to identify other protein components of the cellular lipid homeostasis machinery, perhaps targets or regulators of the NPC1 protein, we have employed a molecular genetic approach in budding yeast, Saccharomyces cerevisiae. We designed a screen to identify gene products that are essential for cell viability only in the absence of cellular sterol esterification. Sterol esterification is a dey determinant of cellular free sterol levels and thus membrane composition in all eukaryotes. We identified a novel gene, ARV1 (termed 'arv' for 'ACAT-Related Enzyme2 Required for Viability'). Yeast strains deleted for the ARV1 gene (arv1Δ) are temperature sensitive, polyene (nystatin, amphotericin B, and filipin) sensitive, and inviable under anaerobic conditions. All three phenotypes are suggestive of gross changes in plasma membrane composition and function. In addition, under aerobic conditions, arv1 cells accumulate 50% of control levels of exogenously supplied C14 cholesterol, suggesting Arv1p may facilitate exogenous sterol transport. The Arv1p amino acid sequence predicts a novel transmembrane protein with high similarity to entries in C. elegans and human databases. We identified a full length cDNA corresponding to human ARV1. Yeast expression plasmids were constructed and found to rescue all arv1 deletion strain growth phenotypes. We propose that hARV1 in human cells might play a role in modulating cellular sterol distribution and plasma membrane lipid composition and that this process may be a feature of NPC disease.

In an embodiment of the above-described isolated nucleic acid molecule which encodes mammalian ARV1p, the nucleic acid is DNA or RNA. In a further embodiment the nucleic acid is cDNA or genomic DNA. In a preferred embodiment the mammalian ARV1 is a human ARV1 (hARV1). In a still further preferred embodiment, the isolated nucleic acid comprises a nucleic acid sequence as set forth in FIG. 6.

This invention provides an isolated nucleic acid which encodes yeast ACAT-Related Enzyme 2 Required for Viability protein (ARV1), wherein the encoded ARV1 protein has the amino acid sequence set forth in FIG. 5.

In an embodiment the above-described isolated nucleic acid which encodes yeast ARV1 comprises a nucleic acid sequence as set forth in FIG. 4.

This invention provides a vector comprising the isolated nucleic acid which encodes mammalian ACAT-Related Enzyme 2 Required for Viability protein (ARV1p), wherein the encoded ARV1p protein has the amino acid sequence set forth in FIG. 7.

In an embodiment of the above-described vector, the vector further comprises a promoter of DNA transcription operatively linked to the nucleic acid. In another embodiment the promoter comprises a bacterial, yeast, insect, plant or mammalian promoter. In another embodiment the vector further comprises a plasmid, cosmid, yeast artificial chromosome (YAC), bacteriophage or eukaryotic viral DNA.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

This invention provides a host vector system for the production of a polypeptide which comprises any of the above-described vectors comprising a promoter of DNA transcription operatively linked to the nucleic acid in a suitable host.

In an embodiment of the above-described host vector system the suitable host is a prokaryotic or eukaryotic cell. In another embodiment the prokaryotic cell is a bacterial cell.

In a further embodiment wherein the eukaryotic cell is a yeast, insect, plant or mammalian cell.

A vector comprising an isolated nucleic acid which encodes yeast ACAT-Related Enzyme 2 Required for Viability protein (ARV1p), wherein the encoded ARV1p protein has the amino acid sequence set forth in FIG. 5.

In an embodiment the above-described vector further comprises a promoter of DNA transcription operatively linked to the nucleic acid. In another embodiment the promoter comprises a bacterial, yeast, insect, plant or mammalian promoter. In additional embodiments the vector further comprising a plasmid, cosmid, yeast artificial chromosome (YAC), bacteriophage or eukaryotic viral DNA.

This invention provides a host vector system for the production of a polypeptide which comprises any of the above-described vectors in a suitable host.

In an embodiment of the above-described host vector system the suitable host is a prokaryotic or eukaryotic cell. In further embodiments of the above-described host vector system, the prokaryotic cell is a bacterial cell. In another embodiment, the eukaryotic cell is a yeast, insect, plant or mammalian cell.

A method for producing a mammalian ACAT-Related Enzyme 2 Required for Vialbility protein (ARV1p) which comprises growing the above-described host vector system under suitable conditions permitting production of the ARV1p and recovering the ARV1p so produced.

This invention provides a method of obtaining a mammalian ACAT-Related Enzyme 2 Required for Viability protein (ARV1p) in purified form which comprises: (a) introducing the above-described vector into a suitable host cell; (b) culturing the resulting cell so as to produce the ARV1p; (c) recovering the ARV1p produced in step (b); and (d) purifying the ARV1p so recovered.

This invention provides a method for producing a yeast ACAT-Related Enzyme 2 Required for Vialbility protein (ARV1p) which comprises growing the above-described host vector system under suitable conditions permitting production of the ARV1p and recovering the ARV1p so produced.

This invention provides a method of obtaining a yeast ACAT-Related Enzyme 2 Required for Vialbility protein (ARV1p) in purified form which comprises: (a) introducing the above-described vector into a suitable host cell; (b) culturing the resulting cell so as to produce the ARV1p; (c) recovering the ARV1p produced in step (b); and (d) purifying the ARV1p so recovered.

This invention provides a purified mammalian ACAT-Related Enzyme 2 Required for Vialbility protein (ARV1p) having the amino acid sequence set forth in FIG. 7.

In an embodiment of the above-described purified mammalian ACAT-Related Enzyme 2 Required for Vialbility protein (ARV1p), the ARV1p is a human ARV1p.

This invention provides a purified yeast ACAT-Related Enzyme 2 Required for Vialbility protein (ARV1p) having the amino acid sequence set forth in FIG. 5.

This invention provides an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 7.

This invention provides an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 5.

One of skill is familiar with conventional techniques for nucleic acid hybridization of oligonucleotides, e.g. Ausubel (21), for example stringent conditions of 65° C. in the presence of an elevated salt concentration. Such conditions are used for completely complementary nucleic acid hybridization, whereas conditions that are not stringent are used for hybridization of nucleic acids which are not totally complementary.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the ARV1 proteins. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding the ARV1 protein is useful as a diagnostic test for any disease process in which levels of expression of the corresponding ARV1 protein is altered. DNA probe molecules are produced by insertion of a DNA molecule which encodes mammalian ARV1 protein or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed herein), electrophoresed, and cut out of the resulting gel. The oligonucleotide probes are useful for 'in situ' hybridization or in order to locate tissues which express this ARV1 gene family, or for other hybridization assays for the presence of these genes or their mRNA in various biological tissues. In addition, synthesized oligonucleotides (produced by a DNA synthesizer) complementary to the sequence of a DNA molecule which encodes an ARV1 protein are useful as probes for this gene, for its associated mRNA, or for the isolation of related genes by homology screening of genomic or cDNA libraries, or by the use of amplification techniques such as the Polymerase Chain Reaction.

In embodiments of any of the above-described oligonucleotides, the nucleic acid may be genomic DNA or cDNA.

This invention provides a method for identifying a chemical compound which is capable of inhibiting ACAT-Related Enzyme 2 Required for Viability protein (ARV1p) which comprises: (a) contacting an isolated ARV1p with the chemical compound under conditions permitting an effect to occur upon contact between the ARV1p and the chemical compound; and (b) determining whether the chemical compound inhibits the activity of the ARV1p so as to identify a chemical compound which is capable of inhibiting ARV1p.

The effect resulting from the contacting the ARV1p with the chemical compound activity may be binding, but is not limited to binding of the ARV1p and the chemical compound.

This invention provides a pharmaceutical composition comprising the chemical compound identified by the above-described method for identifying a chemical compound which is capable of inhibiting ACAT-Related Enzyme 2 Required for Viability protein (ARV1p) in an amount effective to inhibit ARV1p in a subject and a pharmaceutically effective carrier.

This invention provides a method for identifying a chemical compound which is capable of stimulating ACAT-Related Enzyme 2 Required for Viability protein (ARV1p) which comprises: (a) contacting an isolated ARV1p with the chemical compound under conditions permitting an effect to occur upon contact between the ARV1p and the chemical compound; and (b) determining whether the chemical compound stimulates the activity of the ARV1p so as to identify a chemical compound which is capable of stimulating ARV1p.

This invention provides a pharmaceutical composition comprising the chemical compound identified by the above-described method for identifying a chemical compound which is capable of stimulating ACAT-Related Enzyme 2 Required for Viability protein (ARV1p) in an amount effective to stimulate ARV1p in a subject and a pharmaceutically effective carrier.

The ARV1 inhibitor and/or stimulators may be used, i.e. administered to a subject to treat diseases such as hypercholesterolemia, obesity, neurodegeneration, atherosclerosis, hyperlipidemia and to stop cholesterol absorption by the intestine. The experiments herein provide data for stopping cholesterol absorption, i.e. in the absence of ARV1p cholesterol is not absorbed from the external environment of the cells.

As used throghout the specification, subject means any animal, preferably a mammal and most preferably a human.

The invention also provides a pharmaceutical composition comprising a effective amount of the chemical compounds described throughout the specification a pharmaceutically acceptable carrier. In the subject invention an "effective amount" is any amount of the chemical compounds, oligonucleotides, proteins, antibodies, when administered to a subject suffering from a disease or abnormality against which the chemical compounds, oligonucleotides, proteins, antibodies, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The pharmaceutical compositions can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The pharmaceutical compositions can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular pharmaceutical composition in use, the strength of the preparation, the mode of administration, and the advancement of the disease condition or abnormality. Additional factors depending on the particular subject being treated will result in a need to adjust dosages, including subject age, weight, gender, diet, and time of administration.

This invention provides a method of treating a subject who has a disease wherein cellular sterol transport or sterol uptake are defective comprising administering any of the above-described pharmaceutical compositions to the subject.

In a preferred embodiment of the above-described method of treating a subject who has a disease wherein cellular sterol transport or sterol uptake are defective the disease is selected from the group consisting of hypercholesterolemia, obesity, neurodegeneration, atherosclerosis, hyperlipidemia.

In another preferred embodiment the administration of the pharmaceutical composition stops dietary cholesterol absorption by the intestine.

This invention provides a method of redistributing intracellular sterol between plasma membrane and endoplasmic reticulum in a cell of a subject whose sterol transport into the plasma membrane or sterol uptake by the plasma membrane is defective which comprises administering to the cell any of the above-described vectors, thereby increasing ARV1 production in the cell so as to redistribute sterol between the plasma membrane and the endoplasmic reticulum.

The defect in sterol transport into the plasma membrane or sterol uptake by the plasma membrane may be caused by the absence of the ARV1 gene, i.e. nucleic acid encoding for wild-type ARV1p (wild-type may be defines as the normal, unaltered ARV1p) or a mutated nucleic acid encoding for wild-type ARV1p. The mutation in the nucleic acid may be a "loss of function" mutation.

Diagnosis of an intracellular sterol transport defect may be performed by measuring changes in the plasma cholesterol levels of a subject, i.e. before and after a high fat diet. The cells in which redistribution of intracellular sterol transport and sterol uptake take place are, for example, hepatocytes (liver cells) and enterocytes (intestinal) cells.

In a preferred embodiment of the above-described method of redistributing intracellular sterol between plasma membrane and endoplasmic reticulum in a cell of a subject whose sterol transport into the plasma membrane or sterol uptake by the plasma membrane is defective, the defect in sterol transport into the plasma membrane or sterol uptake by the plasma membrane is present in disease selected from the group consisting of hypercholesterolemia, obesity, neurodegeneration, atherosclerosis, hyperlipidemia. In a preferred embodiment of the above-described method the administration of the vector stops intestinal absorption of dietary cholesterol in the subject.

This invention provides a pharmaceutical composition comprising ARV1 protein having the amino acid sequence set forth in FIG. 7 and a pharmaceutically acceptable carrier.

This invention provides a method of treating a subject who has a disease wherein cellular sterol transport or sterol uptake are defective comprising administering a pharmaceutical composition comprising ARV1 protein having the amino acid sequence set forth in FIG. 7 and a pharmaceutically acceptable carrier to the subject so as to restore the sterol transport, sterol uptake or sterol distribution.

In a preferred embodiment of the above-described method of treating a subject who has a disease wherein cellular sterol transport or sterol uptake are defective, the defect in sterol transport into the plasma membrane or sterol uptake by the plasma membrane is present in disease selected from the group consisting of hypercholesterolemia, obesity, neurodegeneration, atherosclerosis, hyperlipidemia. In another preferred embodiment of the above-described method the administration of the pharmaceutical composition stops intestinal absorption of dietary cholesterol in the subject.

This invention provides a method of treating a subject who has a disease wherein cellular sterol transport or sterol uptake are defective comprising administering to cells of the subject the above-described pharmaceutical composition, so as to redistribute intracellular sterol between plasma membrane and endoplasmic reticulum in the cells of the subject and thereby treat the disease.

In a preferred embodiment of the above-described method of treating a subject who has a disease wherein cellular sterol transport or sterol uptake are defective, the defect in sterol transport into the plasma membrane or sterol uptake by the plasma membrane is present in disease selected from the group consisting of hypercholesterolemia, obesity, neurodegeneration, atherosclerosis, hyperlipidemia. In another preferred embodiment of the above-described method, the administration of the pharmaceutical composition stops intestinal absorption of dietary cholesterol in the subject.

This invention provides a method for determining whether elevated levels of intracellular sterol in absence of sterol esterification in a subject are due to ARV1 mutation which comprises: (a) obtaining a nucleic acid sample from the subject; (b) comparing the nucleic acid from the sample with the isolated nucleic acid which encodes mammalian ACAT-Related Enzyme 2 Required for Viability protein (ARV1p), wherein the encoded ARV1p protein has the amino acid sequence set forth in FIG. 7; and (c) determining whether the nucleic acid from the sample of step (a) differs from the isolated nucleic acid encodes mammalian ARV1p, a difference in the nucleic acid from the isolated nucleic acid which encodes ARV1p indicating presence of a mutation in the nucleic acid encoding ARV1 from the sample.

Absence of sterol esterification is determined by an assay to measure deficiency of sterol ester in the plasma of a subject. The above-described method may be used cases of absence of sterol esterification and in all cases of defects in sterol homeostasis.

This invention provides a method for determining whether elevated levels of intracellular sterol in absence of sterol esterification in a subject are due to ARV1 mutation which comprises: (a) obtaining nucleic acid from a sample from the subject; and (b) contacting the nucleic acid of step (a) with an isolated nucleic acid sequence encoding a mutant ARV1 under conditions permitting binding of any nucleic acid from the sample to the nucleic acid sequence encoding a mutant ARV1 so as to form a complex, formation of the complex indicating presence of a mutation in the nucleic acid encoding ARV1 from the sample.

The isolated nucleic acid with which the nucleic acid sample is contacted may be an antisense oligonucleotide of a nucleic acid encoding mutant ARV1p.

Diagnosis may also be performed by sequencing the nucleic acid from a sample of a subject to identify the ARV1 gene and compare the identified sequence with a wild-type sequence so as to determine mutations in the nucleic acid of the subject.

In an embodiment of the above-described method for determining whether elevated levels of intracellular sterol in absence of sterol esterification in a subject are due to ARV1 mutation, the isolated nucleic acid encoding the mutant is labeled with a detectable marker. In another embodiment the detectable marker is a radioactive isotope, a fluorophor or an enzyme. In a further embodiment the nucleic acid from the sample is first bound to a solid matrix before performing step (a). In a still further embodiment the sample comprises plasma or blood cells.

This invention provides a method for treating a subject who has an imbalance in cell sterol levels due to a defect in sterol esterification which comprises introducing an isolated nucleic acid which encodes mammalian ACAT-Related Enzyme 2 Required for Viability protein (ARV1p), wherein the encoded ARV1p protein has the amino acid sequence set forth in FIG. 7, into cells of the subject under conditions such that the nucleic acid expresses ARV1p and the cells obtain sterol from an extracellular source, so as to thereby treat the subject.

This invention provides a method for treating a subject who has an imbalance in sterol levels in cells due to a defect in sterol esterification which comprises administering ARV1p to the subject, such that the ARV1p transports to the cells extracellular sterol, so as to thereby treat the subject.

This invention provides a transgenic nonhuman mammal comprising an isolated nucleic acid which encodes mammalian ACAT-Related Enzyme 2 Required for Viability protein (ARV1p), wherein the encoded ARV1p protein has the amino acid sequence set forth in FIG. 7.

This invention provides a transgenic nonhuman mammal comprising an isolated nucleic acid which encodes mammalian ACAT-Related Enzyme 2 Required for Viability protein (ARV1p), wherein the encoded ARV1p protein has the amino acid sequence set forth in FIG. 7 which is mutated.

Transgenic animals may be used to test compounds and to test interaction with genetic loci to human disease, e.g. the LDL receptor.

This invention provides an antibody directed to an epitope of a purified mammalian ARV1p having the amino acid sequence set forth in FIG. 7.

In an embodiment the mammalian ARV1p is a human ARV1. In further embodiments the above-described antibody may be a polyclonal antibody or a monoclonal antibody.

This invention provides a pharmaceutical composition comprising an amount of an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 7 or of an oligonucleotide of at least 15 nucleotides capable of specifically hybridizing with a unique sequence of complementary nucleotides present within a nucleic acid which encodes a mammalian ACAT-Related Enzyme 2 Required for Vialbility protein (ARV1) having the amino acid sequence set forth in FIG. 5, effective to prevent overexpression of a human ARV1 and a pharmaceutically acceptable carrier capable of passing through a cell membrane.

Diseases wherein an overexpression of ARV1 exists for which the above-described pharmaceutical composition may be used include hyper- or hypo-cholesterolemia.

This invention provides a plant producing seeds whose lipid oils content is altered from the wild-type lipid oils content by a change in the expression of nucleic acid which encodes human ARV1 or plant ARV1.

This invention provides a plant seed whose lipid oils content is altered from the wild-type lipid oils content by a change in the expression of nucleic acid which encode human ARV1 or plant ARV1.

This invention provides a method of altering lipid oils content of a plant seed which comprises introducing into the nucleic acid of the plant seed an isolated nucleic acid encoding plant ARV1p, wherein the encoded plant ARV1p differs from the wild-type plant ARV1, such that the lipid oils content of the plant seed is altered.

This invention provides a pharmaceutical composition comprising lipid oils of a plant seed whose lipid oils content is altered from the wild-type lipid oils content of the plant seed by a change in the expression of nucleic acid which encode ARV1 and a pharmaceutically acceptable carrier.

This invention provides a method for identifying a chemical compound which has antifungal activity which comprises: (a) contacting a yeast cell comprising an isolated nucleic acid which encodes yeast ACAT-Related Enzyme 2 Required for Viability protein (ARV1p), wherein the encoded ARV1p protein is a deletion mutant with the chemical compound under conditions permitting an effect to occur upon contact between the yeast cell and the chemical compound; and (b) determining whether the chemical compound inhibits yeast ARV1p so as to identify a chemical compound which has antifungal activity. The effect may be alteration of intracellular sterol transport, sensitivity to the compound, temperature sensitivity, anaerobic inviability, or a defect in sterol uptake.

In an embodiment of the above-described method, the deletion mutant is arvΔ or arv1-1.

This invention provides a pharmaceutical composition comprising the compound identified by the method for identifying a chemical compound which has antifungal activity and a pharmaceutically acceptable carrier.

This invention provides a method of treating a fungal infection in a subject which comprises administering to the subject the above-described pharmaceutical composition.

This invention provides a method of treating a fungal infection in a subject which comprises administering to the subject the above-described pharmaceutical composition and an antifungal agent.

In an embodiment the antifungal agent is polyene. In a further embodiment the polyene is nystatin, amphotericin B or filipin.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

We screened for mutants of *Saccharomyces cerevisiae* (yeast) that were inviable in the absence of the genes encoding the ACAT-Related Enzymes (Are1p and Are2p)[7,8]. Mutants were identified by their inability to grow in the absence of a plasmid encoding Are2p in an are1 are2 deletion background. We named these mutants arv, for ARE2 Required for Viability. Four complementation groups were obtained. We chose ARV1 for further study because it was the most frequently mutated gene identified in the screen.

Even in the presence of a functional ARE2 gene, arv1-1 strains grow slowly compared to controls and are inviable at 37° C. (FIG. 1a), suggesting that sterol esterification cannot compensate for a critical function of Arv1p which becomes essential at elevated temperature. The ARV1 gene was isolated by complementation of the temperature sensitive phenotype of an arv1-1 strain using a yeast genomic library[9] and shown to be allelic with arv1-1 by conventional methods. Sequencing of PCR-generated DNA from arv1-1 genomic templates identified a stop codon halfway through the predicted ARV1 open reading frame. A complete gene deletion (arv1D) was constructed and found to confer growth characteristics similar to arv1-1 and was used in subsequent studies.

Figure 1B:
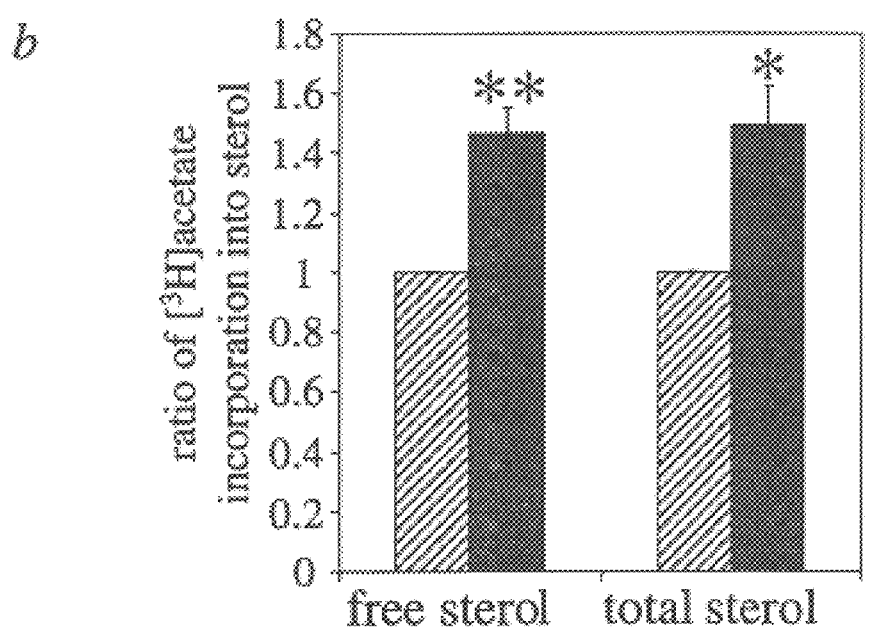

Mutations in sterol trafficking genes may alter membrane sterol levels. arv1D cells are sensitive to nystatin (FIG. 1a), a polyene antibiotic that disrupts membranes in part by interaction with sterols[10]. Nystatin partitioning into membranes is sensitive to both sterol organization and levels[10]. Sterol analysis was thus performed on cells grown in the presence of [$^3$H]acetate; arv1D mutants showed a 50% increase in free and total sterol levels (FIG. 1b). Iodine staining of sterol mass following extraction and thin layer chromatography (TLC) analysis reflected these differences (not shown). These data suggest a role for Arv1p in determining membrane sterol levels.

Figure 1C:
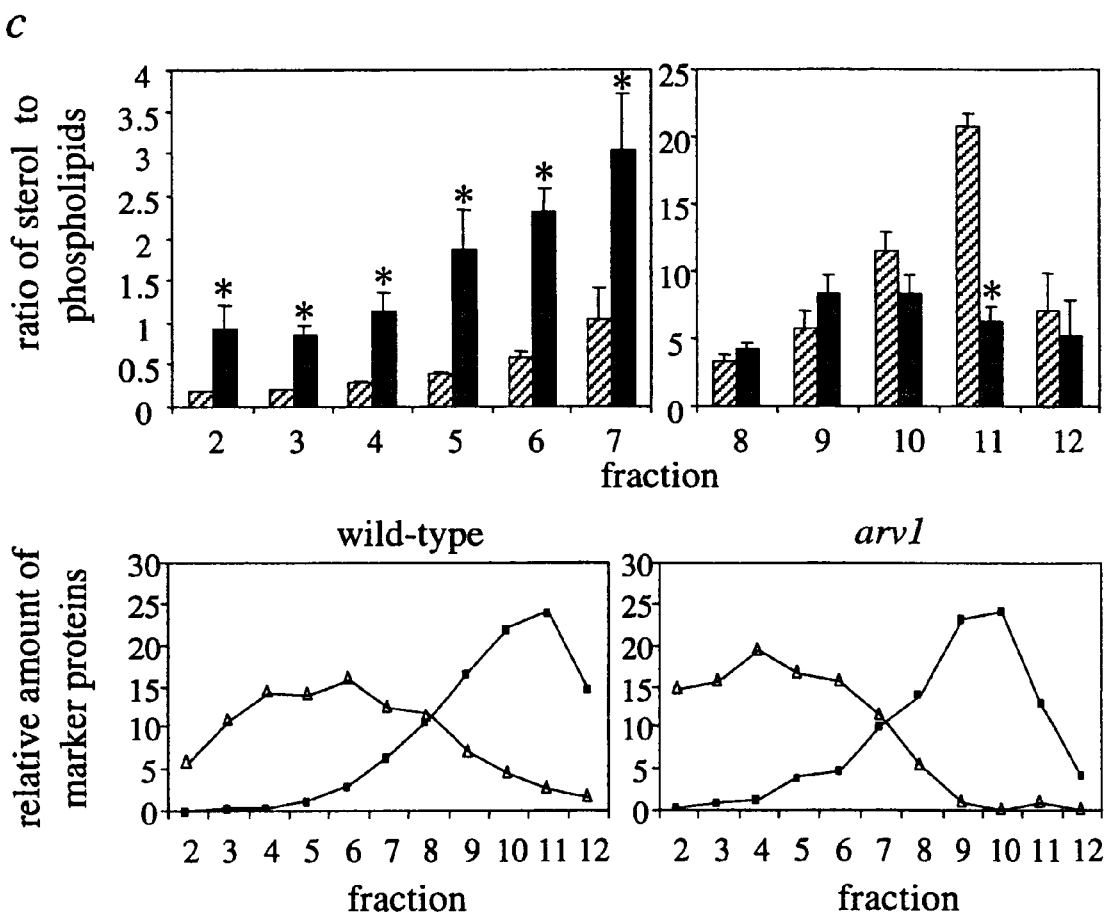

To identify which membranes in arv1D mutants might be accumulating sterol, subcellular fractionation and lipid analyses were performed on membrane preparations from arv1D and wild-type strains. Sterols and phospholipids were assessed by labeling cells to steady state with [$^3$H]acetate and [$^{14}$C]oleate, respectively. The enrichment of free sterol relative to phospholipids distinguishes the PM from other membranes in the cell. The highest sterol-to-phospholipid ratios were seen in the PM fractions of both mutant and wild-type cells, as defined by the PM-specific antigen, Pma1p. However, relative to wild-type cells, arv1D mutants showed elevated sterol in ER and vacuolar membrane fractions suggesting a role for Arv1p in sterol distribution (FIG. 1c).

The essential sterol esterification requirement of arv1 mutants suggests that these cells accumulate toxic levels of free sterol. To control sterol levels in arv1D cells, we utilized anaerobic growth conditions where cells require exogenous sterols and fatty acids[11]. arv1D and wild-type yeast were incubated anaerobically with oleate and a range of ergosterol concentrations. surprisingly, arv1D cells were inviable anaerobically (FIG. 2a), further suggesting a role for Arv1p in sterol homeostasis.

Figures 2A, 2B:
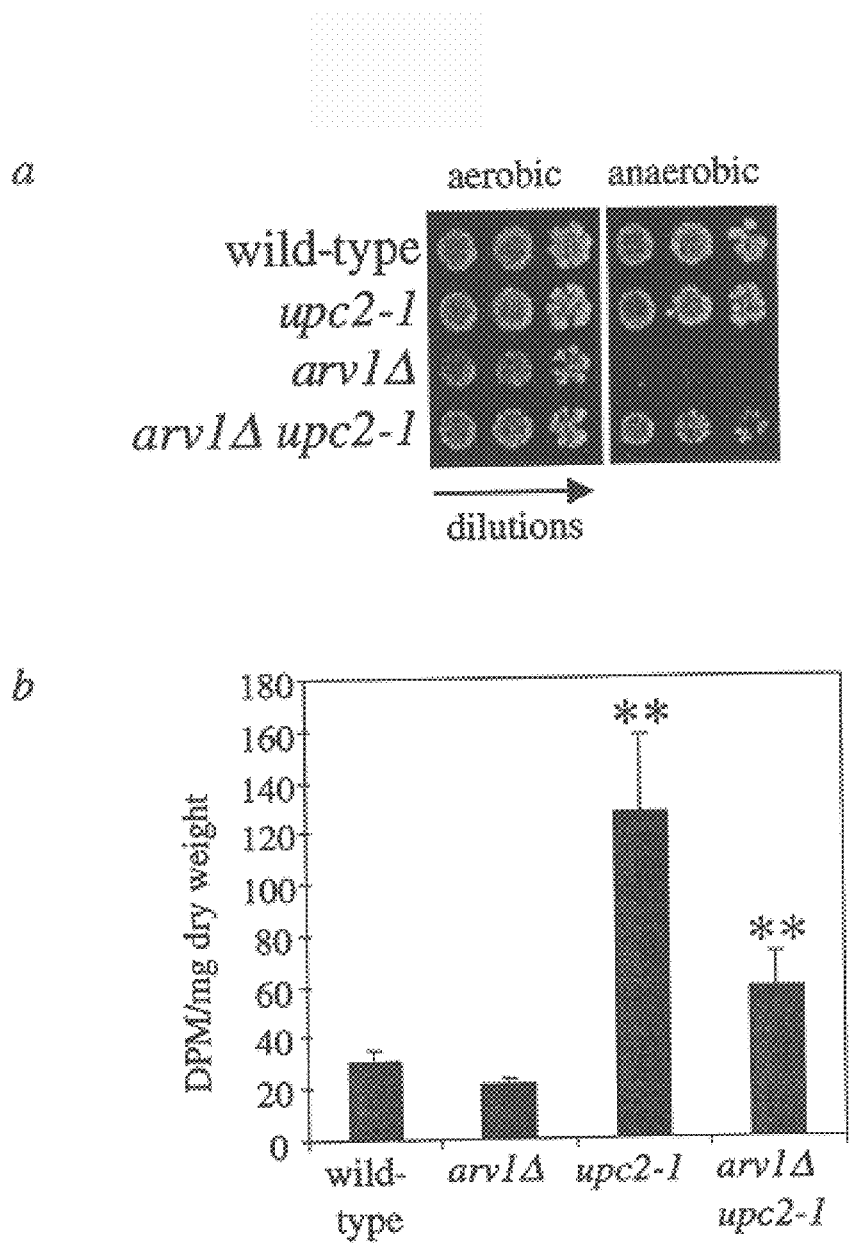
FIGS. 2A–2B Sterol uptake phenotypes.

One explanation for anaerobic inviability of arv1 mutants is that Arv1p mediates sterol uptake. To address this, we constructed arv1D strains carrying a mutation (upc2-1) that allows aerobic sterol uptake[12]. arv1D upc2-1 double mutants accumulated 50% less exogenous [$^{14}$C]cholesterol than upc2-1 cells but similar levels of exogenous [$^3$H]oleate, consistent with a role for ARV1 in sterol uptake (FIG. 2b, and data not shown). Interestingly, sterol uptake in double mutants was significantly elevated compared to wild-type and arv1D controls (FIG. 2b), suggesting upc2-1-mediated ARV1-independent sterol transport mechanisms. Moreover, the upc2-1 mutation suppressed arv1D anaerobic inviability (FIG. 2a). Taken together, these data support the idea that Arv1p plays a critical role in sterol uptake.

The yeast ARV1 gene is predicted to encode a novel 321 amino acid transmembrane protein with a potential zinc-binding motif (FIG. 3a, b). The spacing of the NH$_2$-terminal cysteine residues of Arv1p resembles that seen in zinc ribbons (FIG. 3a), which have been described in general transcription factors where they bind DNA or mediate protein-protein interaction[13]. Interestingly, intragenic complementation between two independent arv1 alleles (arv1-2 and arv1-4) suggests that Arv1p functions as a multimer (not shown). Zinc-binding motifs serve a number of functions in membrane-associated proteins including regulation of small molecule transport[14], recruitment of signaling molecules to PM microdomains[15] and charged lipid binding[16]. Interestingly, endosomes rich in negatively-charged lysobisphosphatidic acid accumulate cholesterol when lumenal zinc concentrations are elevated[17], consistent with a role for zinc-binding proteins in cholesterol homeostasis.

A search of the database of expressed sequence tags (dbEST) revealed Caenorhabditis elegans, Arabidopsis thaliana and ubiquitously expressed human sequences with similarity to Arv1p (FIG. 3a). A full-length human cDNA was sequenced and predicts a 271 amino acid protein (FIG. 3b). The identity of the human, worm, plant and yeast sequences is found in a 61 amino acid NH$_2$-terminal region containing the putative zinc-binding motif and a conserved block of 33 residues which together comprise a novel domain (Arv1 Homology Domain (AHD), ProDom PD038388[18]; FIG. 3a, b)

The sequence conservation of ARV1 between yeast and humans led us to examine whether these genes are functionally equivalent. Expression of the hARV1 coding sequence from the inducible yeast GAL1/10 promoter rescued arv1D growth defects in a galactose-dependent manner (FIG. 3c). Further, hARV1-containing plasmids were obtained in a selection for rescue of arv1D inviability at 37° C. using a human hepatoma (HepG2) cell-derived cDNA yeast expression library[19].

The phenotypes of arv1 mutants (synthetic lethality with are1D are2D, reduced sterol uptake, anaerobic inviability, nystatin sensitivity and subcellular sterol accumulation) are consistent with a role for Arv1p in optimal sterol movement into the PM. These phenotypes could result from defects in plasma membrane microdomains ("rafts"[20]) that may function as sterol acceptors in an Arv1p -dependent fashion. Since human ARV1 can functionally substitute for yeast ARV1, it is likely that Arv1p represents a conserved component of eukaryotic sterol homeostasis. Understanding the biochemical function of these novel proteins will undoubtedly illuminate mechanisms underlying intracellular sterol trafficking.

Methods and Materials
Reagents, Strains, and General Techniques

Yeast extract-peptone dextrose (YEPD), synthetic complete dextrose (SCD), and 5-Fluoro orotic acid (5-FOA; Toronto Research Chemicals) media were prepared as described[21]. Molecular biology reagents were obtained from New England Biolabs, Gibco, and Stratagene. [$^3$H]Acetate (sodium salt), [$^3$H]oleic acid, [1-$^{14}$C]oleic acid, and [4-$^{14}$C] cholesterol were from DuPont-NEN. Other reagents were from Sigma unless noted. Nucleotide sequencing was performed by the Columbia University Cancer Center sequencing facility. Gene-specific oligonucleotides were synthesized by Genset. Yeast strains used in this study were constructed by standard genetic techniques and are isogenic with strain W303-1A unless noted[7]. S. cerevisiae and Escherichia coli (XL1-Blue) transformations were performed as described[22] or by electroporation (BioRad). BBL Gas Jars and GasPak Plus (Becton Dickinson) were used for anaerobiosis according to the manufacturer's instructions.
arv Screen An adenine auxotrophy based colony color sectoring assay was used to identify arv mutants[23]. are1D are2D ade2D ade3D strains of opposite mating type were generated. To facilitate complementation analysis, the are2::LEU2 allele in one parent was converted to are2::leu2::TRP1[24]. Both strains were transformed with plasmid pAT001 (2870 bp PmlI-XhoI fragment of ARE2 at the SalI/NruI sites of plasmid pCH1122[23]), which conferred sterol esterification in are1D are2D strains (data not shown). Parent strains were grown to saturation in SCD-Ura media and exposed to a UV-transilluminator (10–15% survival). Mutants requiring the ARE2 gene were placed in complementation groups by constructing diploids and scoring plasmid retention by colony sectoring or growth on 5-FOA-containing media. Seven arvl alleles were recovered while other complementation groups were represented by four or less alleles.
Isolation of ARV1

Standard techniques[7] were used to isolate and characterize the complementing gene on plasmid p14-5, which rescued all alleles of arvl identified in the screen. Deletion analysis of p14-5 indicated that YLR242C was essential for arv1-1 complementing activity. To confirm that the arv1-1 mutation resided in YLR242C, a strain bearing a LEU2 marked wild-type allele of YLR242C was crossed with an arv1-1 strain. All haploid progeny from this cross were either temperature sensitive or Leu$^+$, indicating linkage of YLR242C and arv1-1.

Construction of arv1 Deletion Allele

Deletion of ARV1 (arv1D) was accomplished using a PCR-generated allele and one-step gene replacements[25]. Oligomers were: 5'KOARV1'(AACGGATGAAGC GCAT-CAAAAAGTAGATATTAGCTGTGATAAACGcatggcaat tcccggggatcg) and 3'KOARV1 (TAAGATTTTTGATAC AAGTAATACTGGATATTTTTTTATTTGCcatggtggtca gctggaattc). Uppercase sequence corresponds to ARV1, lowercase to *Kluyveromyces lactis* URA3. Three independent ARV1/arv1D diploids were confirmed using oligomers: 5'ARV1scr (CGGATGAAGCGCATCAAAAAG), 3'ARV1scr (GTTGGATTGAAATCCCAAGGTGC), and 3'-KLURA3 (gAgCAATgAACCCAATAACgAAATC). Diploid sporulation and tetrad manipulation were performed as described[26]. PCR analysis of genomic DNA from haploid progeny showed 2:2 segregation of the deletion allele. arv1D are1D are2D strains were not recovered in genetic crosses, indicating dependence on sterol esterification for viability of strains carrying the null allele.

Lipid Analyses

Cells grown to mid-log phase in media containing [$^3$H] acetate or [1-$^{14}$C]oleic acid (final concentration 2 μCi/ml and 0.02 μCi/ml, respectively) were washed twice in 0.5% tergitol and once in water and frozen at −70° C. prior to being lyophilized. Lyophilized cell pellets (between 2 and 6 mg) were resuspended in 50 μl of lyticase stock solution (1700 units/ml, in 10% glycerol, 0.02% Na azide) for 15 minutes at 37° C. to remove the cell wall. Treated cell suspensions were incubated at −70° C. for one hour, 37° C. for 15 minutes and vortexed with 200 μl of isopropanol. Lipids were extracted with 5 ml of isopropanol:hexane (1:2) and 5 ml of KCl (2M):MeOH (4:1). The organic layer was collected and the cell suspension was re-extracted with 5 ml of isopropanol:hexane. For measuring the total sterol pools, 3 ml of methanol:KOH (60%) (2:1) were added to the lysed cell/isopropanol suspension, incubated at −70° C. for two hours, and extracted twice with hexane. The organic phases were dried down and analyzed by TLC[27].

Subcellular Fractionation

Membrane preparations were subjected to discontinuous gradient ultracentrifugation as described[28] except that renografin-76 was replaced with renografin-60 (Bracco Diagnostics, a generous gift of Dr. Z. Haskal). 250 μL of each fraction were resuspended in 5 ml H$_2$O:isopropanol (4:1), extracted twice with hexane and analyzed by TLC as before. 15 μl of each fraction was used for SDS-polyacrylamide gel electrophoresis and immunoblot analysis of marker proteins[29].

Analysis of Sterol and Oleate Uptake

The upc2-1 mutation[12] was back-crossed six times into the W303 genetic background and was followed by measuring [4-$^{14}$C]cholesterol accumulation in haploid progeny. Lysed cell suspensions prepared as before from cells grown in media containing 1% tyloxapol:ethanol (1:1), 0.01 μCi/ml [4-$^{14}$C]cholesterol, and 0.25 μCi/ml [$^3$H]oleic acid, were added directly to scintillation fluid followed by counting. PCR amplification from genomic templates and HphI digestion of a 221 bp fragment were also used to identify upc2-1. The upc2-1 mutation (G to A transition at nucleotide 2663[30]) creates a novel HphI restriction site.

Isolation of hARV1

A cDNA was obtained from the IMAGE consortium corresponding to hARV1 (gbAA461156). Both strands of the 1465 bp insert were sequenced. A ~1500 bp EcoRI fragment of the image clone containing the putative hARV1 ORF (Genbank Accession #AF290878) was ligated into pRS416-GP[29] at EcoRI downstream of the GAL1/10 promoter to produce phARV1. Expression of hARV1 in transformants was induced by growth on 3% galactose and confirmed by northern analysis. A human hepatoma (HepG2) cDNA yeast expression library[19] was transformed into an arv1D mutant and viable colonies were selected at 37° C. Sequence and PCR analysis of rescuing plasmids indicated that the majority corresponded to hARV1.

REFERENCES

1. Bloch, K. E. Sterol structure and membrane function. *CRC Crit. Rev. Biochem.* 14, 47–92 (1983).
2. Parks, L. W., Smith, S. J. & Crowley, J. H. Biochemical and physiological effects of sterol alterations in yeast—a review. *Lipids* 30, 227–30 (1995).
3. Jackson, R. L. & Gotto, A. M. J. Hypothesis concerning membrane structure, cholesterol, and atherosclerosis. *Atherosclerosis Reviews* 1, 1–21 (1976).
4. Chang, T.-Y. & Doolittle, G. M. Acyl Coenzyme A: Cholesterol O-Acyltransferase. in *The Enzymes,* Vol. XVI (ed. Boyer, P.) 523–539 (Academic Press, New York, 1983).
5. Xu, X. X. & Tabas, I. Lipoproteins activate acyl-coenzyme A:cholesterol acyltransferase in macrophages only after cellular cholesterol pools are expanded to a critical threshold level. *J Biol Chem* 266, 17040–17048 (1991).
6. Warner, G. J., Stoudt, G., Bamberger, M., Johnson, W. J. & Rothblat, G. H. Cell toxicity induced by inhibition of acyl coenzyme A:cholesterol acyltransferase and accumulation of unesterified cholesterol. *J Biol Chem* 270, 5772–8 (1995).
7. Yang, H. et al. Sterol Esterification in Yeast: A two gene process. *Science* 272, 1353–1356 (1996).
8. Yu, C., Kennedy, N. J., Chang, C. C. Y. & Rothblatt, J. A. Molecular cloning and characterization of two isoforms of *Saccharomyces cerevisiae* acyl-CoA:sterol acyltransferase. *J Biol Chem* 271, 24157–63 (1996).
9. Epstein, C. B. & Cross, F. R. CLB5: a novel B cyclin from budding yeast with a role in S phase. *Genes Dev* 6, 1695–706 (1992).
10. Wang, M. M., Sugar, I. P. & Chong, P. L. Role of the sterol superlattice in the partitioning of the antifungal drug nystatin into lipid membranes. *Biochemistry* 37, 11797–805 (1998).
11. Gollub, E. G., Trocha, P., Liu, P. K. & Sprinson, D. B. Yeast mutants requiring ergosterol as only lipid supplement. *Biochem Biophys Res Commun* 56, 471–7 (1974).
12. Lewis, T. L., Keesler, G. A., Fenner, G. P. & Parks, L. W. Pleiotropic mutations in *Saccharomyces cerevisiae* affecting sterol uptake and metabolism. *Yeast* 4, 93–106 (1988).
13. Hahn, S. & Roberts, S. The zinc ribbon domains of the general transcription factors TFIIB and Brf: conserved functional surfaces but different roles in transcription initiation. *Genes Dev* 14, 719–30 (2000).
14. Loland, C. J., Norregaard, L. & Gether, U. Defining proximity relationships in the tertiary structure of the dopamine transporter. Identification of a conserved glutamic acid as a third coordinate in the endogenous Zn(2+)-binding site. *J Biol Chem* 274, 36928–34 (1999).
15. Hostager, B. S., Catlett, I. M. & Bishop, G. A. Recruitment of CD40 TRAF2 and TRAF3 to membrane microdomains during CD40 signaling. *J Biol Chem* (2000).
16. Kutateladze, T. G. et al. Phosphatidylinositol 3-phosphate recognition by the FYVE domain. *Mol Cell* 3, 805–11 (1999).
17. Kobayashi, T. et al. Late endosomal membranes rich in lysobisphosphatidic acid regulate cholesterol transport [see comments]. *Nat Cell Biol* 1, 113–8 (1999).

18. Corpet, F., Gouzy, J. & Kahn, D. The ProDom database of protein domain families. *Nucleic Acids Res* 26, 323–6 (1998).
19. Schild, D., Brake, A. J., Kiefer, M. C., Young, D. & Barr, P. J. Cloning of three human multifunctional de novo purine biosynthetic genes by functional complementation of yeast mutations. *Proc Natl Acad Sci U S A* 87, 2916–20 (1990).
20. Bagnat, M., Keranen, S., Shevchenko, A. & Simons, K. Lipid rafts function in biosynthetic delivery of proteins to the cell surface in yeast. *Proc Natl Acad Sci USA* 97, 3254–9 (2000).
21. Ausubel, F. M. et al. *Current Protocols in Molecular Biology*, (John Wiley & Sons, New York, 1998).
22. Ito, H., Fukuda, Y., Murata, K. & Kimura, A. Transformation of intact yeast cells treated with alkali cations. *J. Bacteriol.* 153, 163–168 (1983).
23. Kranz, J. E. & Holm, C. Cloning by Function: An alternative approach for identifying yeast homologs of genes from other organisms. *Proc. Natl. Acad. Sci. USA* 87, 662 9–6633 (1990).
24. Cross, F. R. 'Marker swap' plasmids: convenient tools for budding yeast molecular genetics. *Yeast* 13, 647–53 (1997).
25. Erdeniz, N., Mortensen, U. H. & Rothstein, R. Cloning-free PCR-based Allele Replacement Methods. *Genome Research* 7, 1174 (1998).
26. Sherman, F. & Hicks, J. Micromanipulation and Dissection of Asci. in *Methods in Enzymology*, Vol. 194 (eds. Guthrie, C. & Fink, G. R.) 21–37 (Academic Press, 1991).
27. Freeman, C. P. & West, D. Complete separation of lipid classes on a single thin-layer plate. *J Lipid Res* 7, 324–7 (1966).
28. Schandel, K. A. & Jenness, D. D. Direct evidence for ligand-induced internalization of the yeast alpha-factor pheromone receptor. *Mol Cell Biol* 14, 7245–55 (1994).
29. Yang, H., Cromley, D., Wang, H., Billheimer, J. T. & Sturley, S. L. Functional Expression of a cDNA to Human acyl-CoA:cholesterol acyltransferase (ACAT) in Yeast; Species-Dependent Substrate Specificity and Inhibitor Sensitivity. *J. Biol. Chem.* 272, 3980–3985 (1997).
30. Crowley, J. H., Leak, F. W., Jr., Shianna, K. V., Tove, S. & Parks, L. W. A mutation in a purported regulatory gene affects control of sterol uptake in *Saccharomyces cerevisiae*. *J Bacteriol* 180, 4177–83 (1998).
31. Altschul, S. F. et al. Gapped BLAST and PSI-BLAST: a new generation of protein database search programs. *Nucleic Acids Res.* 25, 3389–3402 (1997).
32. Rost, B. PHD: predicting 1D protein structure by profile based neural networks. in *Meth. in Enzym.*, Vol. 266 (ed. Doolittle, R.) 525–539 (1996).

What is claimed is:

1. An isolated nucleic acid which encodes mammalian ACAT-Related Enzyme 2 Required for Viability protein (ARV1p), wherein the encoded ARV1p protein has the amino acid sequence set forth in FIG. 7 (SEQ ID NO 14).

2. The isolated nucleic acid molecule of claim 1, wherein the nucleic acid is DNA or RNA.

3. The isolated nucleic acid of claim 1, wherein the nucleic acid is cDNA or genomic DNA.

4. The isolated nucleic acid of claim 1 comprising a nucleic acid sequence as set forth in FIG. 6 (SEQ ID NO: 3).

5. A vector comprising the isolated nucleic acid of claim 1.

6. The vector of claim 5 further comprising a promoter of DNA transcription operatively linked to the nucleic acid.

7. The vector of claim 6, wherein the promoter comprises a bacterial, yeast, insect, plant or mammalian promoter.

8. The vector of claim 7, further comprising a plasmid, cosmid, yeast artificial chromosome (YAC), bacteriophage or eukaryotic viral DNA.

9. A host vector system for the production of a polypeptide which comprises the vector of claim 6 in a host cell.

10. The host vector system of claim 9, wherein the host cell is a prokaryotic or eukaryotic cell.

11. The host vector system of claim 10, wherein the prokaryotic cell is a bacterial cell.

12. The host vector system of claim 10, wherein the eukaryotic cell is a yeast, insect, plant or mammalian cell.

13. A method for producing a mammalian ACAT-Related Enzyme 2 Required for Vialbility protein (ARV1p) which comprises growing the host vector system of claim 9 under suitable conditions permitting production of the ARV1p and recovering the ARV1p so produced.

14. A method of obtaining a mammalian ACAT-Related Enzyme 2 Required for Viability protein (ARV1p) in purified form which comprises:

(a) introducing the vector of claim 9 into a host cell;

(b) culturing the resulting cell so as to produce the ARV1p;

(c) recovering the ARV1p produced in step (b); and (d) purifying the ARV1p so recovered.

* * * * *